United States Patent [19]

Stevens et al.

[11] Patent Number: 5,290,788
[45] Date of Patent: Mar. 1, 1994

[54] INDOLE DERIVATIVES AS ANTIALLERGY AND ANTIINFLAMMATORY AGENTS

[75] Inventors: Rodney W. Stevens, Handa; Hiromasa Morita, Chita; Masami Nakane, Nagoya, all of Japan

[73] Assignee: Pfizer Inc., New York, N.Y.

[21] Appl. No.: 848,941

[22] PCT Filed: Oct. 1, 1991

[86] PCT No.: PCT/US91/07045
§ 371 Date: Apr. 21, 1992
§ 102(e) Date: Apr. 21, 1992

[30] Foreign Application Priority Data

Oct. 3, 1990 [JP] Japan ................... 2-265687

[51] Int. Cl.$^5$ ............... C07D 403/06; C07D 403/12; A61K 31/475; A61K 31/47
[52] U.S. Cl. ...................... 514/314; 514/339; 546/174; 546/176; 546/273
[58] Field of Search ............ 546/174, 273, 176; 514/314, 339

[56] References Cited

U.S. PATENT DOCUMENTS 4,695,581  9/1987  Suzuki et al. .............. 514/415
4,758,586  7/1988  Chan et al. ................ 514/415

FOREIGN PATENT DOCUMENTS 137163   4/1985  European Pat. Off. .
0419049  3/1991  European Pat. Off. .
2058140  5/1972  Fed. Rep. of Germany .
1228848  4/1971  United Kingdom .

OTHER PUBLICATIONS

Allais, et al., Eur. J. Med. Chem. 1975-10, No. 2, 187-199.
Juby, et al., Journal of Med. Chem. 12 (1969), May, pp. 396-401.
Zhao, et al., J. Org. Chem. 56:3001-3006 (1991).

Primary Examiner—David B. Springer
Attorney, Agent, or Firm—Peter C. Richardson; Gregg C. Benson; James T. Jones

[57] ABSTRACT

Alkoxy substituted indole derivatives as inhibitors of lipoxygenase and useful as antiallergy and antiinflammatory agents.

15 Claims, No Drawings

INDOLE DERIVATIVES AS ANTIALLERGY AND ANTIINFLAMMATORY AGENTS

BACKGROUND OF THE INVENTION

This invention relates to novel indole derivatives. The compounds of the present invention inhibit the action of lipoxygenase enzyme, and are useful in the treatment or alleviation of inflammatory diseases, allergy and cardiovascular diseases in mammals. This invention also relates to pharmaceutical compositions comprising such compounds.

Arachidonic acid is known to be the biological precursor of several groups of endogenous metabolites, prostaglandins including prostacyclins, thromboxanes and leukotrienes. The first step of the arachidonic acid metabolism is the release of esterified arachidonic acid and related unsaturated fatty acids from membrane phospholipids, via the action of phospholipase. Free fatty acids are then metabolized either by cylooxygenase to produce the prostaglandins and thromboxanes or by lipoxygenase to generate hydroperoxy fatty acids which may be further converted to the leukotrienes. Leukotrienes have been implicated in the pathophysiology of inflammatory diseases, including rheumatoid arthritis, gout, asthma, ischemia reperfusion injury, psoriasis and inflammatory bowel disease. Any drug that inhibits lipoxygenase is expected to provide significant new therapy for both acute and chronic inflammatory conditions.

Recently, several review articles on lipoxygenese inhibitors have been reported. (see H. Masamune and L. S. Melvin, Sr., Annual Reports in Medicinal Chemistry 24 (1989) pp. 71-80 (Academic), B. J. Fitzsimmons and J. Rokach Leukotriens and Lipoxygenases (1989) pp. 427-502 (Elsevier).

Compounds having structural features similar to those of the present invention are disclosed in European Patent Publication Nos. 288962A, 313295A and 313296A and in Japanese Application Publication No. 104584.

SUMMARY OF THE INVENTION

The compounds of the present invention are of the formula

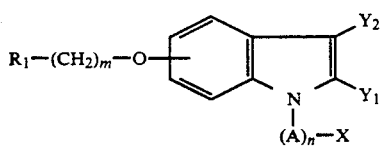

and the pharmaceutically acceptable acid addition salts thereof, where $R_1$ is naphthyl, quinolyl, pyridyl, 2-phenylthiazolyl, 4,6-dimethylpyrimidinyl, benzothienyl, 5-tetrazolyl, or alkylureido of two to six carbon atoms; m is an integer of 1 to 2; $Y_1$ is hydrogen or alkyl of one to four carbon atoms; $Y_2$ is hydrogen, alkyl of one to four carbon atoms, pyridylvinylene, benzoyl or substituted benzoyl where said substituent is methyl, methoxy, fluoro, chloro or trifluoromethyl, benzyl or substituted benzyl where said substituent is methyl, methoxy, fluoro, chloro or trifluoromethyl; A is $-CH_2-$ or $-C(O)-$; n is an integer of 0 to 3; and X is hydrogen, alkyl of one to three carbon atoms, pyridyl, hydroxy, thienyl, carboxy, alkoxycarbonyl of two to four carbon atoms, amino, benzyloxycarbonylamine, phenyl or substituted phenyl wherein said substituent is methyl, methoxy, carboxy, alkoxycarbonyl of two to four carbon atoms, fluoro, chloro or trifluoromethyl with the proviso that when A is $-C(O)-$, n is 1 and when D is 0, X is hydrogen.

A preferred group of compounds are those wherein R is 2-quinolyl; m is 1; $Y_2$ is hydrogen or alkyl of one to four carbon atoms and A is $-CH_2-$. Especially preferred within this group are 1-(3-methoxybenzyl)-5-(2-quinolylmethoxy)-indole, 1-(3-picolyl)-5-(2-quinolylmethoxy)indole, 1-(3-[3-pyridyl]-n-propyl)-5-(2-quinolylmethoxy)indole, 3-ethyl-1-(3-picolyl)-2-n-propyl-5-(2-quinolylmethoxy)-indole, 1-(3-hydroxypropyl)-5-(2-quinolylmethoxy)indole, 3-(5-[2-quinolylmethoxy]indol-1-yl)propionic acid, 4-([5-(2-quinolylmethoxy)indol-1-yl]methyl)benzoic acid and 1-n-heptyl-5-(2-quinolylmethoxy)indole.

A second preferred group of compounds are those wherein $R_1$ is 2-pyridyl, m is 1, $Y_1$ and $Y_2$ are each hydrogen and A is $-CH_2-$. Especially preferred within this group are 1-(4-chlorobenzyl)-5-(2-pyridylmethoxy)indole and 1-(3-picolyl)-5-(2-pyridylmethoxy)indole.

The present invention also includes a method for treating an allergic or inflammatory condition in a mammal which comprises administering to said mammal an antiallergic or antiinflammatory effective amount of a compound of formula I.

The present invention includes a pharmaceutical composition for the treatment of allergic or inflammatory conditions which comprises an antiallergic or antiinflammatory effective amount of a compound of formula I or a pharmaceutically acceptable salt together with a pharmaceutically acceptable carrier.

Finally, the present invention includes a process for preparing a compound of formula I where $R_1$, m, $Y_1$, $Y_2$, n, A and X are as defined which comprises either reacting a compound of the formula

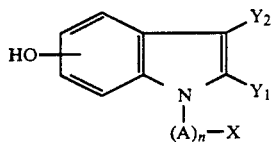

with a compound of the formula $R_1(CH_2)_m-Z$ 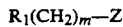

where Z is chloro, bromo or iodo in a reaction-inert solvent containing one equivalent of a base until the reaction is substantially complete or reacting a compound of the formula

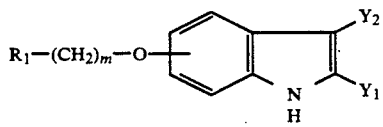

with a compound of the formula $X-(A)_n-Z$ 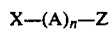

in a reaction-inert solvent containing one equivalent of a base until the reaction is substantially complete and optionally a) reacting a product where $R_1$ is —CN with sodium azide and aluminum chloride, b) reducing a product where $R_1$ is —CN with lithium aluminum hydride and reacting the product with an alkylisocyanate having two to six carbon atoms, c) hydrolyzing a product where X is alkoxycarbonyl having two to four carbon atoms with an aqueous solution of an inorganic base, d) reducing a product where X is ethoxycarbonyl with lithium aluminum hydride, e) reducing a product where X is —CN with lithium aluminum hydride and reacting the product with benzyloxycarbonly chloride or f) hydrolyzing a product where X is alkoxycarbonylphenyl said alkoxy having one to four carbon atoms with an aqueous solution of an inorganic base.

The term "pharmaceutically-acceptable salt" used herein means a non-toxic cation, including those of alkaline earth metals such as sodium, lithium, calcium and magnesium, and organic cation bases of ammoniums and amines, or non-toxic phosphate or acid phosphate, acetate, citrate, fumarate, gluconate, lactate, maleate, succinate tartrate, methanesulfonate, benzenesulfonate, toluenesulfonate, and formate salts thereof.

DETAILED DESCRIPTION OF THE INVENTION

The compounds of the present invention wherein the indole nitrogen is either substituted or unsubstituted can be prepared by alkylation of the appropriate hydroxyindole with $R_1$—$(CH_2)_m$—Z where Z is a halogen or a conventional leaving group. There action is conducted in the present of an appropriate base. Preferred basic agents employed in this reaction are inorganic bases such as, but not limited to, sodium hydroxide, potassium hydroxide, sodium hydride and n-butyl lithium or an organic base such as, but not limited to, sodium methoxide or potassium tert-butoxide. Suitable reaction-inert solvents are acetone, N,N-dimethylformamide, dimethylsulfoxide, diethyl ether, tetrahydrofuran and the like or an optional mixture thereof. The reaction is usually conducted under cooling at ambient temperature or under heating, reaction times of from 30 minutes to a several hours being common. Product of formula I thus obtained is isolated by standard methods and purification can be achieved by conventional means, such as recrystallization and chromatography.

Compounds of the present invention can also be prepared by alkylation of an alkoxy substituted indole which is unsubstituted at the 1-position. This alkylation reaction is also conducted in the presence of an appropriate base. Preferred basic agents employed in this reaction are inorganic bases such as, but not limited to, sodium hydroxide, potassium hydroxide, sodium hydride and n-butyl lithium or an organic base such as, but not limited to, pyridine. Suitable reaction-inert solvents are acetone, N,N-dimethylformamide, dimethylsulfoxide, diethyl ether, tetrahydrofuran and the like or an optional mixture thereof. The reaction is usually conducted under cooling, at ambient temperature or under heating, reaction times of from 30 minutes to a several hours being common. The product is isolated by standard methods and purification can be achieved by conventional means, such as recrystallization and chromatography.

In addition to the main sequences for preparing the compounds of the present invention there are several secondary reactions applicable to the synthesis of certain compounds. For example, when $R_1$ is alkylureido the compounds where R is —CN are first reduced with lithium aluminum hydride followed by the reaction of the amine product with an appropriate alkyl isocyanate.

To prepare those compounds where $R_1$ is 5-tetrazolyl, the product where $R_1$ is —CN is reacted with sodium azide and aluminum chloride.

Hydrolysis of the product wherein X is alkoxycarbonyl using an aqueous inorganic base provide the compounds of the present case where X is carboxy.

Reducing the product where X is alkoxycarbonyl with lithium aluminum hydride provides those compounds where X is hydroxy.

Reduction of the product where X is —CN provides the compounds where X is amino. Further reaction of the amino compounds with benzyloxycarbonyl chloride provides those compounds where X is benzoylcarbonylamino.

Finally hydrolysis of the product where X is phenyl substituted with alkoxycarbonyl provides those compounds where X is phenyl substituted by carboxy. This reaction is readily carried out with an aqueous inorganic base.

The starting reagents needed to synthesize the compounds of the present invention are either readily available or can be prepared by reaction sequences known to those skilled in the art.

The pharmaceutically-acceptable salts of the novel compounds of the present invention are readily prepared by contacting said compounds with a stoichiometric amount of, in the case of a non-toxic cation, an appropriate metal hydroxide or alkoxide or amine in either aqueous solution or a suitable organic solvent; or, in the case of a non-toxic acid salt, an appropriate mineral or organic acid in either aqueous solution or suitable organic solvent. The respective salt can then be obtained by precipitation or by evaporation of the solvent.

The compounds of this invention inhibit the activity of the lipoxygenase enzyme. This inhibition has been demonstrated by an assay using rat peritoneal cavity resident cells which determines the effect of said compounds on the metabolism of arachidonic acid.

All of the compounds were tested according to the methods described in Jap. J. Inflammation 7:145–150, 1987, "Synthesis of leukotrienes by peritoneal macrophages", and those were shown to possess the efficacy of inhibiting lipoxygenase activity.

In this test some preferred compounds indicate low IC50 values, in the range of 0.1 to 30 $\mu$M, with respect to lipoxygenase inhibition.

The ability of the compounds of the present invention to inhibit lipoxygenase enzyme make them useful for controlling the symptoms induced by the endogenous metabolites arising from arachidonic acid in a mammalian subject. The compounds are therefore valuable in the prevention and treatment of such disease states in which the accumulation of arachidonic acid metabolites are the causative factor, e.g, allergic bronchial asthma, skin disorders, rheumatoid arthritis, osteoarthritis and thrombosis.

Thus, the compounds of formula and their pharmaceutically-acceptable salts are of particular use in the treatment or alleviation of inflammatory diseases, allergy and cardiovascular diseases in a human subject as well in the inhibition so the lipoxygenase enzyme.

For treatment of the various conditions described above, the compounds and their pharmaceutically-acceptable salts can be administered to a human subject either alone, or, preferably, in combination with pharmaceutically-acceptable carriers of diluents in a pharmaceutical composition, according to standard pharmaceutical practice. A compound can be administered a variety of conventional routes of administration including orally, parentally and by inhalation. When the compound are administered orally, the dose range will be from about 0.1 to 20 mg/kg per day in single or divided doses. If parenteral administration is desired, then an effective dose will be from 0.1 to 1.0 mg/kg body weight of the subject to be treated per day. In some instances it may be necessary to use dosages outside these limits, since dosage will necessarily vary according to the age, weight and response of the individual patient as well as the severity of the patients symptoms and the potency of the particular compound being administered.

For oral administration, the compounds of the invention and their pharmaceutically-acceptable salts can be administered, for example, in the form of tablets, powders, lozenges, syrups or capsules, or as an aqueous solution or suspension. In the case of tablets for oral use, carriers which are commonly used include lactose and corn starch. Further, lubricating agents, such as magnesium stearate, are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solution of the active ingredient are usually prepared, and the pH of the solutions should be suitably adjusted and buffered. For intravenous use, the total concentration of solute should be controlled to make the preparation isotonic.

The present invention is illustrated by the following examples. However, it should be understood that the invention is not limited to the specific details of these examples. Proton nuclear magnetic resonance spectra (NMR) were measured at 270 MHz unless otherwise indicated and peak positions are expressed in parts per million (ppm) downfield from tetramethylsilane. The peak shapes are denoted as follows: s, singlet; d, doublet; t, triplet; q, quartet; m, multiplet; br, broad.

EXAMPLE 1

5-(2-Quinolylmethoxy)indole

A mixture of 5-hydroxyindole (5.0 g), 2-chloromethylquinoline (7.0 g) and potassium carbonate (10.0 g) in N,N-dimethyl formamide (50 ml) was stirred at 80° C. for 4 hours. The cooled mixture was poured into water, and extracted with ethyl acetate. The combined organic layers were washed with water, dried over magnesium sulfate, and concentrated in vacuo. The crude product was recrystallized from ethanol to yield the title product (5.0 g), m.p. 134°–137° C.

NMR (CDCl$_3$): 8.15(1H,d,J=8 Hz), 8.10(1H,d,J=8 Hz), 7.70–7.98(3H,m), 7.55(1H,t,J=8 Hz), 7.15–7.30(3H,m), 7.00(1H,dd,J=9 and 2 Hz), 6.44(1H,d,J=3 Hz), 5.44(1H,s)

EXAMPLE 2

1-(4-Chlorobenzyl)-5-(2-quinolylmethoxy)indole

To a suspension of 60% sodium hydride (0.47 g) in N,N-dimethylformamide solution (20 ml) cooled to 0° C. was added a N,N-dimethylformamide solution (10 ml) of 5-(2-quinolymethoxy)indole (2.5 g), followed by the addition of an N,N-dimethylformamide solution (5 ml) of 4-chlorobenzyl chloride (1.54 g). The mixture was stirred at this temperature for 30 minutes, poured into water, and extracted with ethyl acetate, and concentrated in vacuo. The crude product was chromatographed on silica gel using 50%-ethyl acetate in n-hexane as eluent to yield 1-(4-chlorobenzyl)-5-(2-quinolylmethoxy)indole (3.0 g), m.p. 102°–104° C.

NMR(CDCl$_3$) 8.16(1H,d,J=8 Hz), 8.08(1H,d,J=8 Hz), 7.81(1H,d,8 Hz), 7.70–7.76(2H,m), 7.54(1H,t,J=8 Hz), 6.95–7.25(8H,m), 6.43(1H,d,J=3 Hz), 5.42(2H,s), 5.24(2H,s)

EXAMPLES 3–13

Employing the procedure of Example 2 and starting with the appropriate materials, the following compounds were prepared:

1-(4-Chlorobenzoyl)-5-(2-quinolylmethoxy)indole. m.p. 140° C.

NMR(CDCl$_3$): 8.30(1H,d,J=8 Hz), 8.20(1H,d,J=8 Hz), 8.10(1H,t,J=8 Hz), 7.83(1H,d,J=8 Hz), 7.65–7.76(4H,m), 7.48–7.56(3H,m), 7.13–7.21(3H,m), 6.53(1H,d,J=3 Hz), 5.47(2H,s)

1-(4-Chlorobenzyl)-4-(2-quinolylmethoxy)indole, m.p.

NMR(CDCl$_3$): 8.18(1H,d,J=8 Hz), 8.09(1H,d,J=8 Hz), 7.74–7.85(3H,m), 7.55(1H,t,J=7 Hz), 7.25–7.28(2H,m), 6.87(1H,d,J=8 Hz), 6.79(1H,d,J=3 Hz), 6.59(1H,d,J=7 Hz), 5.56(2H,s), 5.29(2H,s)

1-(3-Methoxybenzyl)-5-(2-quinolylmethoxy)indole. m.p. 119°–120° C.

NMR(CDCl$_3$): 8.16(1H,d,J=8 Hz), 8.08(1H,d,J=8 Hz), 7.81(1H,d,J=8 Hz), 7.70–7.76(2H,m), 7.53(1H,t,J=8 Hz), 7.16–7.23(3H,m), 7.08(1H,d,J=3 Hz), 6.96(1H,dd,J=9 and 3 Hz), 6.78(1H,dd,J=9 and 3 Hz), 6.41–6.69(2H,m), 6.42(1H,d,J=3 Hz), 5.42(2H,s), 5.24(2H,s), 3.72(3H,s)

1-(3-Picolyl)-5-(2-quinolylmethoxy)indole, m.p. 119°–120° C.

NMR(CDCl$_3$): 8.50–8.53(2H,m), 8.17(1H,d,J=8 Hz), 7.82(1H,d,J=8 Hz), 7.70–7.77(2H,m), 8.09(1H,d,J=8 Hz)7.51–7.57(1H,m), 7.14–7.33(4H,m), 7.08(1H,d,J=8 Hz), 6.98(1H,dd,J=9 and Hz), 6.45(1H,d,J=3 Hz), 5.43(2H,s), 5.30(2H,s)

1-(4-Chlorobenzyl)-5-(2-pyridylmethoxy)indole. m.p. 85° C.

NMR(CDCl$_3$): 8.58–8.61(1H,m), 7.70(1H,dt,J=7 and 2 Hz), 7.57(1H,d,J=7 Hz), 7.00–7.28(8H,m), 6.9–6.96(1H,m), 6.45(1H,d,J=3 Hz), 5.25(4H,s)

1-(4-Chlorobenzyl)-5-(2-naphthylmethoxy)indole, m.p. 100°–101° C.

NMR(CDCl$_3$): 7.83–7.92(4H,m), 7.57(1H,d,J=7 Hz), 7.46–7.49(2H,m), 7.23–7.27(3H,m), 6.96–7.13(5H,m), 6.45(1H,d,J=3 Hz), 5.26(2H,s), 5.25(2H,s)

1-(3-Picolyl)-5-(2-pyridylmethoxy)indole. m.p. 71°–72.5° C.

NMR(CDCl$_3$): 8:59(1H,m), 8.51(1H,s), 7.70(1H,t,J=7 Hz), 7.56(1H,d,J=7 Hz), 7.09–7.31(5H,m), 6.94(1H,dd,J=9 and 2 Hz), 6.47(1H,d,J=3 Hz), 5.30(2H,s) 5.25(2H,s)

1-[3-(3-Pyridyl)propyl]-5-(2-quinolylmethoxy)indole, m.p. 80°-80.5° C.

NMR(CDCl₃): 8.43-8.47(2H,m), 8.17(1H,d,J=8 Hz), 8.08(1H,d,J=8 Hz), 7.81(1H,d,J=7 Hz), 7.70-7.76(2H,m), 7.51-7.57(1H,m), 7.45(1H,dt,J=7 and 2 Hz), 7.18-7.26(3H,m), 6.99-7.05(2H,m), 6.38(1H,d,J=3 Hz), 5.44(2H,s), 4.12(2H,t,J=7 Hz), 2.60(2H,t,J=7 Hz), 1.61-2.20(2H,m)

5-(2-Quinolylmethoxy)-1-[2-(2-thienyl)ethyl]indole, m.p. 134°-136° C.

NMR(CDCl₃): 8.17(1H,d,J=8 Hz), 8.10(1H,d,J=8 Hz), 7.81(1H,d,J=8 Hz), 7.71-7.76(2H,m), 7.54(1H,t,J=8 Hz), 7.14-7.22(2H,m), 7.01(1H,dd,J=9 and 2 Hz) 6.68-6.91(2H,m), 6.67(1H,d,J=3 Hz), 6.34(1H,d,J=3 Hz), 5.43(2H,s), 4.34(2H,t,J=7 Hz), 3.31(2H,t,J=7 Hz)

1-(ethoxycarbonylmethyl)-5-(2-quinolylmethoxy)indole, m.p. 89°-92° C.

NMR(CDCl₃): 8.17(1H,d,J=8 Hz), 8.09(1H,d,J=8 Hz), 7.70-7.84(3H,m), 7.51-7.57(1H,m), 7.15-7.19(2H,m), 7.00-7.06(2H,m], 6.43(1H,d,J=3 Hz), 5.43(2H,s), 4.79(2H,s), 4.20(2H,q,J=7 Hz), 1.24(3H,t,J=7 Hz)

1-n-Heptyl-5-(2-quinolylmethoxy)indole. m.p. 37°-39° C.

NMR(CDCl₃): 8.16(1H,d,J=8 Hz), 8.09(1H,d,8 Hz), 7.77(1H,d,8 Hz), 7.70-7.76(2H,m), 7.53(1H,t,J=8 Hz), 7.17-7.25(2H,m), 6.99-7.06(2H,m), 6.35(1H,d,J=3 Hz), 5.43(2H,s), 4.06(2H,t,J=7 Hz), 1.78-1.83(2H,m), 1.25-1.29(8H,m), 0.86(3H,t,J=7 Hz)

EXAMPLE 14

1-(4-Chlorobenzyl)-3-[2-(3-pyridyl)ethenyl]-5-(2-quinolylmethoxy)indole

A. 1-(4-chlorobenzyl -3-formyl-5-(2-quinolylmethoxy)indole

To a solution of phosphorus oxychloride (2.9 ml) and N,N-dimethylformamide (10 ml) was added a N,N-dimethylformamide solution of 1-(4-chlorobenzyl)-5-(2-quinolylmethoxy)indole (4.2 g) at 0° C. The mixture was stirred overnight at ambient temperature and then poured into an aqueous sodium bicarbonate solution. The separated solid was washed with water and then ether to yield 1-(4-chlorobenzyl-3-formyl-5-(2-quinolylmethoxy)-indole (3.0 g) which was used without further purification.

B. 1-(4-Chlorobenzyl)-3-2-(3-pyridyl)ethenyl -5-(2-quinolylmethoxy)indole

A suspension of sodium hydride (60%-oil suspension, 0.39 g), 3-picolyl-triphenylphosphonium chloride (2.55 g) and N,N-dimethylformamide was stirred for 20 minutes, followed by the addition of 1-(4-chlorobenzyl)-3-formyl-5-(2-quinolylmethoxy)indole (3.0 g). The mixture was stirred for an additional 10 hours and then poured into water-ethyl acetate (50% v/v). The organic layer was separated, washed with brine, dried over magnesium sulfate, and concentrated in vacuo. The resultant crude product was purified by chromatography on silica gel using 50%-ethyl acetate in n-hexanes as eluent to yield 1-(4-chlorobenzyl)-3-(2-(3-pyridyl)ethenyl)-5-(2-quinolylmethoxy)indole (1.0 g), m.p. 169°-171° C.

NMR(CDCl₃): 8.65(1H,d,J=2 Hz), 8.43(1H,dd,J=5 and 2 Hz), 8.20(1H,d,J=8 Hz), 8.10(1H,d,J=8 Hz), 7.70-7.85(4H,m), 7.52-7.58(2H,m), 7.22-7.36(3H,m), 7.01-7.15(4H,m), 6.89(1H,d,J=17 Hz), 5.50(2H,s), 5.25(2H,s)

EXAMPLE 15

3-(3-Methoxybenzyl)-5-(2-quinolylmethoxy)indole

A. 2-(3-methoxyohenyl)-2-(3-[5-hydroxyindolyl])-1,3-dithiane

To a mixture of 5-hydroxyindole (3.3 g) and 2-methylthio-2-(3-methoxyphenyl)-1,3-dithiane (7.17 g) in chloroform (50 ml), trifluoroborate etherate (6.4 ml) was added at ambient temperature. The mixture was stirred for 2 hours and then washed with water, dried over magnesium sulfate, and concentrated in vacuo. The crude product was chromatographed on silica gel using 30% ethyl acetate in n-hexanes as eluent to yield 2-(3-methoxyphenyl)-2-(3-(5-hydroxyindolyl))-1,3-dithiane (3.8 g).

B. 3-(3-methoxybenzyl)-5-hydroxyindole

A mixture of 2-(3-methoxyphenyl)-2-(3-(5-hydroxyindolyl))-1,3-dithiane (3.0 g) and Raney-Ni (5.0 g) in ethanol was refluxed for 3 hours. The cooled mixture was filtered and concentrated in vacuo. The crude product was chromatographed on silica gel using 30%-ethyl acetate in hexanes to yield 3-(3-methoxybenzyl)-5-hydroxyindole (1.2 g).

C. 3-(3-methoxybenzyl)-5-(2-quinolylmethoxy)indole

A mixture of 3-(3-methoxybenzyl)-5-hydroxyindole (1.22 g), 2-chloroquinoline (1.2 g) and potassium carbonate (2.4 g) in N,N-dimethylformamide (20 ml) was stirred at 80° C. for 4 hours. The cooled reaction mixture was poured into water, and extracted with ethyl acetate. The combined organic layers were washed with water, dried over magnesium sulfate, and concentrated in vacuo. The resultant crude product was recrystallized from benzene to yield 3-(3-(methoxybenzyl)-5-(2-quinolymethoxy)indole (1.2 g), m.p. 122°-123° C.

NMR(CDCl₃): 8.15(1H,d,J=8 Hz), 8.07(1H,d,J=8 Hz), 7.87(1H,brs), 7.8l(1H,d,8 Hz), 7.70-7.76(2H,m), 7.54(1H,t,J=7 Hz), 7.25(1H,d,J=8 Hz), 7.05-7.11(2H,m), 6.97(1H,dd,J=9 and 2 Hz), 6.90(1H,d,J=2 Hz), 6.80(1H,d,J=8 Hz), 6.77(1H,d,J=2 Hz), 6.66(1H,d,J=9 and 2 Hz), 5.39(2H,s), 4.00(2H,s), 3.73(3H,s)

EXAMPLE 16

3-Benzoyl-5-(2-quinolylmethoxy)indole

To a mixture of 5-(2-quinolymethoxy)indole (1.7 g) and benzoyl chloride (1.0 ml) in 1,2-dichloroethane (15 ml) was added aluminum chloride (3.8 g) in one portion at ambient temperature. The solution was stirred for 5 hours, and then poured into aqueous sodium bicarbonate solution (pH 9) and ethyl acetate added. The organic layer was separated, washed with water, dried over magnesium sulfate and concentrated in vacuo. The crude product was recrystallized from ethyl acetate/ethanol to yield the title product (0.73 g), m.p. 214°-216° C.

NMR(CDCl₃): 11.98(1H,br.s), 8.42(1H,d,J=8 Hz), 8.04(1H,d,J=8 Hz), 8.00(1H,d,J=8 Hz), 7.84–7.91(2H,m), 7.71–7.82(4H,m), 7.44–7.65(6H,m), 7.06(1H,dd,J=9 and 2 Hz), 5.42(2H,s)

EXAMPLES 17–20

Starting with the appropriate reagents, and employing the procedure of Example 2, the following compounds were prepared:

3-Benzoyl-1-(4-chlorobenzyl)-5-(2-quinolylmethoxy)indole, m.p. 150°–153° C.

NMR(CDCl$_3$): 8.20(1H,d,J=8 Hz), 8.12(1H,s), 8.11(1H,d,J=8 Hz), 7.72–7.83(5H,m), 7.45–7.58(5H,m), 7.29(1H,d,J=8 Hz), 7.03–7.18(4H,m), 5.47(2H,s), 5.30(2H,s)

3-Ethyl-2-propyl-1-(3-picolyl)-5-(2-quinolylmethoxy)indole, m.p. 68.5°–69.5° C.

NMR(CDCl$_3$): 8.46(1H,dd,J=5 and 1Hz), 8.38(1H,d,J=1 Hz), 8.18(1H,d,J=8 Hz), 8.08(1H,d,J=8 Hz), 7.70–7.84(3H,m), 7.53(1H,td,J=8 and 1Hz), 7.20(1H,d,J=2 Hz) 7.07–7.14(2H,m) 6.99(1H,d,J=9 Hz), 6.87(1H,dd,J=9 and 2 Hz), 5.44(2H,s), 5.28(2H,s), 2.60–2.74(4H,m), 1.45–1.53(2H,m), 1.20(3H,t,J=7 Hz), 0.94(3H,t,=7 Hz)

1-(N-Phthaloylaminopropyl)-5-(2-quinolylmethoxy)indole Methyl 4([5-(2-quinolylmethoxy)indol-1-yl]methyl)benzoate

EXAMPLE 21

3-Ethyl-2-propyl-5-(2-quinolylmethoxy)indole

A. 3-ethyl-5-methoxy-2-propylindole

A mixture of 4-methoxyphenyl hydrazine hydrochloride (3.0 g), 4-heptanone (1.94 g), and sulfuric acid (1.3 ml) in ethanol (10 ml) was stirred at 10° C. for 3 hours. The cooled mixture was poured into aqueous sodium bicarbonate solution, such that the pH was adjusted to 9. The solution was extracted with ethyl acetate, the organic layer separated, washed with water, dried over magnesium sulfate, and concentrated in vacuo. The crude product was chromatographed on silica gel using 25%-ethyl acetate in n-hexanes as eluent to yield 3-ethyl-5-methoxy-2-propylindole (3.22 g).

B. 3-ethyl-5-hydroxy-2-propylindole

3-Ethyl-5-methoxy-2-propyl indole (2.92 g) in 15 ml of hydrogen bromide acetic acid solution was heated at 100° C. for 4 hours. The cooled solution was poured into an aqueous sodium bicarbonate solution (100 ml) and ethyl acetate with stirring. The separated organic layer was washed with water, dried over magnesium sulfate, and concentrated in vacuo. The crude product was chromatographed on silica gel using 30% ethyl acetate in n-hexanes as eluent to yield 3-ethyl-5-hydroxy-2-propyl indole (2.7 g).

C. 3-ethyl-2-propyl-5-(2-quinolylmethoxy)indole

Starting with the product of Example 21B and following the procedure of Example 1, the titled product was prepared, m.p. 91° C.

NMR(CDCl$_3$): 8.17(1H,d,J=8 Hz), 8.08(1H,d,J=8 Hz), 7.50–7.84(5H,m), 7.17(1H,d,J=9 Hz), 7.14(1H,d,J=2 Hz), 6.89(1H,dd,J=9 and 2 Hz), 2.60–2.70(4H,m), 1.62–1.71(2H,m), 1.16(3H,t,J=7 Hz), 0.97(3H,t,J=7 Hz)

EXAMPLE 22

1-(3-Hydroxylpropyl)-5-(2-quinolylmethoxyl)indole

A. 1-ethoxycarbonylethyl-5-benzyloxyindole

To a suspension of 60% sodium hydride (15 g) in dimethylformamide (30 ml) was added a N,N-dimethylformamide solution of 5-benzyloxyindole (5.0 g) at 0° C. After 15 minutes a solution of ethyl-3-chloropropionate (3.1 ml) in N,N-dimethylformamide was added dropwise and the reaction mixture stirred for a further 5 hours at ambient temperature. The reaction mixture was poured into water and extracted with ethyl acetate. The organic layer was washed with water, dried over magnesium sulfate, and concentrated in vacuo. The residue was chromatographed on silica gel eluting with 15%-ethyl acetate in n-hexanes to yield the title product (6.81 g).

B. 1-ethoxycarbonylethyl-5-hydroxyindole

A mixture of 1-ethoxycarbonyl-5-benzyloxy indole (26.2 g) and Palladium hydroxide (2.0 g) in ethyl acetate (300 ml) was stirred under a hydrogen atmosphere overnight. The mixture was filtered and the filtrate was concentrated in vacuo to yield 1-ethoxycarbonylethyl-5-hydroxy indole (17.1 g).

C. 1-ethoxycarbonylethyl-5-(2-quinolylmethoxy)indole

1-Ethoxycarbonylethyl-5-(2-quinolymethoxy)indole was prepared from 1-ethoxycarbonylethyl-5-hydroxyindole according to the procedure outlined in Example 1.

D. 1-( 3-hydroxypropyl)-5-(2-quinolylmethoxylindole

To a suspension of lithium aluminium hydride (1.73 g) in 150 ml of tetrahydrofuran cooled to 0° C. was added dropwise a solution of 1-ethoxycarbonylethyl-5-(2-quinolymethoxy)indole (13.3 g) in 50 ml of tetrahydrofuran. After addition was complete the reaction mixture was warmed to room temperature and stirred at this temperature for a further 5 hours. The mixture was cooled to 0° C. and a 5% sodium hydroxide solution added carefully to decompose excess lithium aluminium hydride. Insoluble materials were removed by filtration and washed copiously with ether. The combined organic layers were dried over magnesium sulfate and then concentrated in vacuo. The resultant crude product was chromatographed on silica gel eluting with 25% ethylacetate in n-hexanes to yield 1-(3-hydroxypropyl)-5-(2-quinolymethoxy)indole (3.3 g), m.p. 92°–94° C.

NMR(CDCl$_3$): 8.17(1H,d,J=8 Hz), 8.10(1H,d,J=8 Hz), 7.81(1H,d,J=8 Hz), 7.70–7.76(2H,m), 7.53(1H,d,J=8 Hz), 7.28(1H,d,J=8 Hz), 7.17(1H,d,J=3 Hz), 7.07(1H,d,J=3 Hz), 7.01(1H,dd,J=9 and 2 Hz), 6.37(1H,d,J=3 Hz), 5.43(2H,s), 4.25(2H,t,J=7 Hz), 3.60(2H,q,J=7 Hz), 2.00–2.10(2H,m), 1.33(1H,m)

In a similar manner 1(3-hydroxypropyl)-5-([2-phenyl-4-thiazolyl]methoxy)indole, m.p.103°–105° C.

NMR(CDCl$_3$): 7.95–7.99(2H,m), 7.43–7.47(3H,m), 7.28–7.34(2H,m), 7.21(1H,d,J=2 Hz), 7.10(1H,d,J=3 Hz) 6.98(1H,dd,J=9 and 2 Hz), 6.41(1H,d,J=3 Hz), 5.31(2H,s), 4.25(2H,m), 3.58–3.64(2H,m), 2.04–2.08(2H,m), 1.31(1H,br.s) and 1-(3-hydroxypropyl)-5-(4.6-dimethyl-2-pyrimidymethoxy)indole hydrochloride monohydrate. m.p. 104°–110° C.

NMR(CDCl$_3$): 7.34(1H,d,J=9 Hz), 7.24–7.29(2H,m), 7.08(1H,d,J=2 Hz), 6.83(1H,d,J=9 and 2 Hz), 6.30(1H,d,J=3 Hz), 5.11(2H,s), 4.17(2H,t,J=7 Hz), 3.35(2H,t,J=7 Hz), 2.49(3H,s), 2.44(3H,s), 1.83-1.88(2H,m) were prepared.

EXAMPLE 23

3-[5-(2-Quinolylmethoxy)indol-1-yl]propionic acid

A mixture of 1-ethoxycarbonylethyl-5-(2-quinolylmethoxy)indole (2.0 g) and lithium hydroxide monohydrate (0.9 g) in aqueous tetrahydrofuran was refluxed for 3 hours. The cooled mixture was extracted with ethyl acetate and the organic layer was washed with water, dried over magnesium sulfate, and concentrated in vacuo. The crude product was chromatographed on silica gel eluting with 50%-ethyl acetate in n-hexanes to yield the titled product, m.p. 157°-160° C.

NMR(DMSO-$d_6$): 8.19(1H,d,J=8 Hz), 8.13(1H,d,J=8 Hz), 7.81(1H,d,J=8 Hz), 7.71-7.77(2H,m), 7.52-7.57(1H,m), 7.25-7.28(1H,m), 7.09-7.13(2H,m), 6.98(1H,dd,J=9 and 2 Hz), 6.35(1H,d,J=3 Hz), 5.36(2H,s), 4.43(2H,t,J=7 Hz), 2.87(2H,t,J=7 Hz)

EXAMPLE 24

1-13-(Benzyloxycarbonylamino)propyl]-5-(2-quinolylmethoxy)indole

A. 1-aminopropyl-5-(2-quinolylmethoxy)indole

A mixture of 1-(N-phthaloylaminopropyl)-5-(2-quinolymethoxy) indole (1.67 g), hydrazine hydrate (0.2 ml) in ethanol (10 ml) was refluxed for 1.5 hours. The cooled mixture was concentrated in vacuo, and then purified by chromatography on silica gel using 25%-ethyl acetate in n-hexanes as eluent to yield the titled product (10 g).

B.
1-[3-(benzyloxycarbonylamino)propyl]-5-(2-quinolylmethoxy)indole

A mixture of 1-aminopropyl-5-(2-quinolylmethoxy)-indole (1.0 g) and benzyloxycarbonyl chloride (1.0 ml) in toluene was heated at 100° C. for 15 minutes. The cooled solution was concentrated in vacuo and the resultant product purified by chromatographed on silica gel using 30%-ethyl acetate in n-hexanes as eluent to yield 1-(3-(benzyloxycarbonylamino-n-propyl)-5-(2-quinolylmethoxy)-indole (0.27 g), m.p. 109°-111° C.

NMR (CDCl$_3$): 8.16(1H,d,J=8 Hz), 8.10(1H,d,J=8 Hz), 7.8I(1H,d,J=8 Hz), 7.70-7.76(2H,m), 7.54(1H,t,J=8 Hz), 7.30-7.34(5H,m), 7.17-7.23(2H,m), 6.98-7.06(2H,s), 6.36(1H,d,J=3 Hz,) 5.43(2H,s), 5.09(2H,s), 4.70(1H,br.s), 4.13(2H,t,J=7 Hz), 3.15-3.18(2H,m), 2.03(2H,t,J=7 Hz)

EXAMPLE 25

4-([5-(2-Quinolylmethoxy)indol-1-yl]methyl)benzoic acid

Starting with methyl 4-([5-(2-Quinolylmethoxy)indol-1-yl]methyl)benzoate and employing the hydrolysis procedure of Example 23, the titled product was prepared, m.p. 212°-216° C.

NMR(DMSO-$d_6$): 8.38(1H,d,J=8 Hz), 8.10(1H,d,J=8 Hz), 7.97(1H,d,J=8 Hz), 7.85(2H,d,J=8 Hz), 7.79(1H,t,J=7 Hz), 7.68(1H,d,8=Hz,) 7.57(1H,d,J=7 Hz), 7.45(1H,d,J=3 Hz), 7.30(1H,d,J=9 Hz), 7.18-7.22(3H,m), 6.89(1H,dd,J=9 and 3 Hz), 6.38(1H,d,J=3 Hz), 5.46(2H,s), 5.35(2H,s)

EXAMPLE 26

1-(4-chlorobenzyl)-5-(4-pyridylmethoxy)indole

To a suspension of sodium hydride (0.2 g, 60%) in N,N-dimethylformamide (30 ml) cooled to 0° C. was added a solution of 1-(4-chlorobenzyl)-5-hydroxy)indole (1.0 g) in N-dimethylformamide. The reaction mixture was stirred for 15 minutes, and then a solution of 4-chloromethylpyridine (0.76 g) in 10 ml of N,N-dimethylformamide was added dropwise and stirring continued for a further 30 minutes. The mixture was poured into water and extracted with ethyl acetate. The combined organic extracts was washed with water dried over magnesium sulfate and then concentrated in vacuo. The resultant residue was chromatographed on silica gel using 50% ethyl acetate in n-hexanes as eluent to yield 1-(4-chlorobenzyl)-5-(4-pyridylmethoxy)indole (0.70 g), m.p. 105°-107° C.

NMR(CDCl$_3$): 8.59-8.62(2H,m), 7.37-7.39(2H,m), 7.23-7.28(2H,m), 7.09-7.16(3H,m), 7.00-7.04(2H,m), 6.90(1H,dd,J=9 and 2 Hz), 6.45(1H,d,J=3 Hz), 5.25(2H,s), 5.12(2H,s)

In a similar manner 1-(4-chlorobenzyl)-5-(2-benzothienylmethoxy)indole, m.p. 145°-147° C.

NMR(CDCl$_3$): 7.27-7.83(2H,m), 7.08-7.36(9H,m), 7.00(1H,d,J=8 Hz), 6.92(1H,dd,J=9 and 2 Hz), 6.47(1H,d,J=3 Hz), 5.34(2H,s), 5.24(2H,s) was prepared.

EXAMPLE 27

1-(4-Chlorobenzyl)-5-(-5-tetrazolylmethoxy)indole

A. 1-(4-Chlorobenzyl)-5-cyanomethoxy)indole

The title product was prepared from 1-(4-chlorobenzyl)-5-hydroxyindole and bromoacetonile using the procedure of Example 1.

B. 1-(4-Chlorobenzyl)-5-(-5-tetrazolylmethoxy)indole

A mixture of (1-(4-Chlorobenzyl)indol-5-yl)oxyacetonitrile (2.0 g), sodium azide (0.55 g) and ammonium chloride (0.43 g) in N,N-dimethylformamide (15 ml) were heated at 140° C. for 5 hrs. The cooled mixture was poured into 5%-hydrochloride solution. The solution was extracted with ethyl acetate and the separated organic layer was washed with water, dried over magnesium sulfate, and concentrated in vacuo. The crude product was recrystallized from ethanol to yield the titled product, m.p. 162°-163° C.

NMR(DMSO-$d_6$): 7.48(1H,d,J=3 Hz), 7.16-7.38(6H,m), 6.84(1H,dd,J=9 and 2 Hz), 6.41(1H,d,J=3 Hz), 5.44(2H,s), 5.38(2H,s)

EXAMPLE 28

1-Butyl-3-(2-[(1-[4-chlorobenzyl]indol-5-yl)oxyl]ethyl)urea

To a mixture of 1-(4-chlorobenzyl)-5-(aminoethoxy)indole (1.0 g) in pyridine (I ml), butyl isocyanate (0.5 ml) was added at ambient temperature. After stirring for 15 minutes, excess pyridine was evaporated in vacuo and the residue recrystallized from ethanol to yield the title product, m.p. 163°-164° C.

NMR(CDCl$_3$): 7.07-7.26(5H,m), 7.00(2H,d,J=9 Hz), 6.80(1H,dd,J=9 and 2 Hz), 6.46(1H,d,J=3 Hz), 5.24(2H,s), 4.49(1H,br.s), 4.40(1H,br.s), 4.00-4.06(2H,m), 3.57-3.63(2H,m), 3.12-3.20(2H,m), 1.30-1.50(4H,m), 0.90(3H,t,J=7 Hz)

EXAMPLE 29

4-(2-Quinolylmethoxy)indole

A mixture of 4-hydroxyindole (3.0 g), 2-chloromethylquinoline (5.06 g), potassium carbonate (9.0 g) in dimethylformamide (20 ml) was heated at 80° C. for 2 hours. The solids were filtered and the filtrate diluted with water and extracted with ethyl acetate. The organic phase was separated, washed with a brine solution, dried over magnesium sulfate and concentrated in vacuo. The residue was chromatographed on silica gel using hexane-ethyl acetate (5:1;V:V) and then recrystallized from ethanol, 5.1 g, m.p. 143°-144° C.

NMR(CDCl$_3$) 8.2(1H, br.s), 8.17(1H,d,J=8.1Hz), 8.09(1H,d,J=8.8 Hz), 7.71-7.85(3H,m), 7.54(1H,t,J=7.3 Hz), 7.17-7.18(1H,m), 7.03-7.10(2H,m), 6.80-6.82(1H,m), 6.58-6.61(1H,m), 5.56(2H,s)

We claim:

1. A compound of the formula

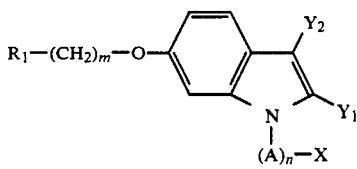

and the pharmaceutically acceptable salts thereof wherein R$_1$ is quinoylyl or pyridyl; m is an integer of 1 to 2; Y$_1$ is hydrogen, or alkyl having one to four carbon atoms; Y$_2$ is hydrogen, alkyl having one to four carbon atoms, pyridylvinylene, benzoyl or substituted benzoyl where said substituent is methyl, methoxy, chloro, fluoro or trifluoromethyl, benzyl or substituted benzyl wherein said substituent is methyl, methoxy, chloro, fluoro or trifluoromethyl; A is —CH$_2$— or —C(O)—; n is an integer of 0 to 3; and X is hydrogen, alkyl having one to three carbon atoms, pyridyl, hydroxy, thienyl, carboxy, alkoxycarbonyl of two to four carbon atoms, amino, benzyloxycarbonylamino, phenyl or substituted phenyl wherein aid substituent is methyl, carboxy, alkoycarbonyl of two to four carbon atoms, methoxy, fluoro, chloro or trifluoromethyl with the proviso that when A is —C(O)—, n is 1 and when n is 0, X is hydrogen.

2. A compound of claim 1, wherein R$_1$ is 2-quinolyl; m is 1; Y$_2$ is hydrogen or alkyl having one to four carbon atoms; and A is —CH$_2$—.

3. The compound of claim 2, 1-(3-methoxybenzyl)-5-(2-quinolylmethoxy)indole.

4. The compound of claim 2, 1-(3-picolyl)-5-(2-quinolylmethoxy)indole.

5. The compound of claim 2, 1-(3-[3-pyridyl]-n-propyl)-5-(2-quinolylmethoxy)indole.

6. The compound of claim 2, 3-ethyl-1-(3-picolyl)-2-n-propyl-5-(2-quinolylmethoxy)indole.

7. The compound of claim 2, 1-(3-hydroxypropyl)-5-(2-quinolylmethoxy)indole.

8. The compound of claim 2, 3-(5-[2-quinolylmethoxy]indol-1-yl)propionic acid.

9. The compound of claim 2, 4-([5-(2-quinolylmethoxy)indol-1-yl]methyl)benzoic acid.

10. The compound of claim 2, 1-n-heptyl-5-(2-quinolylmethoxy)indole.

11. The compound of claim 1, wherein R$_1$ is 2-pyridyl; m is 1; Y$_1$ and Y$_2$ are each hydrogen; and A is —CH$_2$—.

12. The compound of claim 11, 1-(4-chlorobenzyl)-5-(2-pyridylmethoxy)indole.

13. The compound of claim 1, 1-(3-picolyl)-5-(2-pyridylmethoxy)indole.

14. A method for treating a mammal with an allergic or inflammatory condition which comprises administering to said mammal an antiallergic or antiinflammatory effective amount of a compound according to claim 1.

15. A pharmaceutical composition for the treatment of allergic or inflammatory conditions which comprises an antiallergic or antiinflammatory effective amount of a compound according to claim 1 or its pharmaceutically acceptable salt together with a pharmaceutically acceptable carrier.